(12) United States Patent
Hsieh et al.

(10) Patent No.: US 9,414,792 B2
(45) Date of Patent: *Aug. 16, 2016

(54) COMPUTED TOMOGRAPHY SYSTEM WITH DYNAMIC BOWTIE FILTER

(71) Applicant: The Board of Trustees of the Leland Stanford Junior University, Palo Alto, CA (US)

(72) Inventors: Scott Hsieh, Anaheim, CA (US); Norbert J. Pelc, Los Altos, CA (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/301,195

(22) Filed: Jun. 10, 2014

(65) Prior Publication Data

US 2014/0294141 A1 Oct. 2, 2014

Related U.S. Application Data

(63) Continuation-in-part of application No. 14/125,926, filed as application No. PCT/US2012/042469 on Jun. 14, 2012.

(60) Provisional application No. 61/498,175, filed on Jun. 17, 2011, provisional application No. 61/589,245, filed on Jan. 20, 2012, provisional application No. 61/833,719, filed on Jun. 11, 2013.

(51) Int. Cl.
*A61B 6/06* (2006.01)
*G21K 1/10* (2006.01)
(Continued)

(52) U.S. Cl.
CPC .............. *A61B 6/4035* (2013.01); *A61B 6/405* (2013.01); *G02B 5/201* (2013.01); *G21K 1/10* (2013.01);
(Continued)

(58) Field of Classification Search
CPC .......... A61B 6/00; A61B 6/06; A61B 6/4035; A61B 6/405; A61B 6/44; G21K 1/00; G21K 1/02; G21K 1/10; G21K 2201/00; G02B 5/20; G02B 5/201; G02B 5/22; G02B 5/223; G02B 26/00; G02B 26/02; G02B 26/023
USPC ............ 378/4, 16, 20, 62, 91, 145, 156–159, 378/204, 210; 359/885, 889–892
See application file for complete search history.

(56) References Cited

U.S. PATENT DOCUMENTS 3,660,664 A 5/1972 Pasmeg
4,445,226 A 4/1984 Brody
(Continued)

FOREIGN PATENT DOCUMENTS

JP 07008483 A * 1/1995 ............... A61B 6/14
JP 2010-511857 4/2010
(Continued)

OTHER PUBLICATIONS

Office Action dated Jul. 31, 2015 from U.S. Appl. No. 14/125,926.
(Continued)

*Primary Examiner* — Anastasia Midkiff
(74) *Attorney, Agent, or Firm* — Beyer Law Group LLP

(57) ABSTRACT

A CT apparatus for scanning an object is provided. An x-ray source is provided, wherein the x-ray source provides a collimated x-ray beam with a cross-section. A plurality of wedges is provided between the source and object. An actuator is connected to the wedges for moving the wedges substantially perpendicular to the length of the cross-section of the collimated x-ray beam. An x-ray detector is located on an opposite side of the object from the x-ray source and is for detecting x-rays that pass through the object and the plurality of wedges. A gantry rotates the x-ray source, the plurality of wedges, and the x-ray detector around an axis of rotation. A detection system measures the relative position of the plurality of wedges. The detection system comprises an optical sensor and a plurality of optical markers, where each wedge has at least one optical marker attached.

14 Claims, 12 Drawing Sheets

(51) Int. Cl.
*G02B 5/22* (2006.01)
*G02B 5/20* (2006.01)
*A61B 6/00* (2006.01)
*A61B 6/03* (2006.01)

(52) U.S. Cl.
CPC .. *A61B 6/032* (2013.01); *A61B 6/06* (2013.01); *A61B 6/44* (2013.01); *A61B 6/583* (2013.01); *G02B 5/22* (2013.01)

(56) References Cited

U.S. PATENT DOCUMENTS

| | | | |
|---|---|---|---|
| 4,916,727 | A | 4/1990 | Sheridan |
| 4,980,904 | A | 12/1990 | Sones et al. |
| 5,247,559 | A | 9/1993 | Ohtsuchi et al. |
| 5,335,260 | A | 8/1994 | Arnold |
| 5,625,665 | A | 4/1997 | Fokkink et al. |
| 6,359,969 | B1 | 3/2002 | Shmaenok |
| 6,501,828 | B1 * | 12/2002 | Popescu .......... 378/150 |
| 6,920,203 | B2 | 7/2005 | Short et al. |
| 7,076,029 | B2 | 7/2006 | Toth et al. |
| 7,260,182 | B2 | 8/2007 | Toth et al. |
| 7,330,535 | B2 | 2/2008 | Arenson et al. |
| 7,433,443 | B1 | 10/2008 | Tkaczyk et al. |
| 7,630,477 | B2 | 12/2009 | Toth et al. |
| 7,634,045 | B2 | 12/2009 | Popescu |
| 7,706,508 | B2 | 4/2010 | Arenson et al. |
| 7,796,725 | B1 * | 9/2010 | Wu et al. .......... 378/43 |
| 8,412,308 | B2 * | 4/2013 | Goldbach .......... 600/424 |
| 9,006,677 | B2 | 4/2015 | Al-Sadah et al. |
| 2003/0198319 | A1 | 10/2003 | Toth et al. |
| 2003/0199757 | A1 | 10/2003 | Toth et al. |
| 2004/0105526 | A1 * | 6/2004 | Zhang et al. .......... 378/205 |
| 2004/0179646 | A1 | 9/2004 | Li et al. |
| 2004/0225222 | A1 * | 11/2004 | Zeng et al. .......... 600/476 |
| 2005/0013411 | A1 | 1/2005 | Yahata et al. |
| 2005/0031084 | A1 | 2/2005 | Toth et al. |
| 2005/0089137 | A1 | 4/2005 | Toth et al. |
| 2005/0089146 | A1 | 4/2005 | Toth et al. |
| 2006/0198496 | A1 | 9/2006 | Toth et al. |
| 2009/0218521 | A1 | 9/2009 | Sogard et al. |
| 2010/0061513 | A1 | 3/2010 | Muto |
| 2010/0308229 | A1 | 12/2010 | Bertram et al. |
| 2011/0206259 | A1 * | 8/2011 | Mistretta et al. .......... 382/131 |
| 2014/0192950 | A1 | 7/2014 | Pelc et al. |
| 2014/0328453 | A1 | 11/2014 | Hsieh et al. |

FOREIGN PATENT DOCUMENTS

| | | |
|---|---|---|
| JP | 4550179 | 7/2010 |
| WO | WO 2012/174246 | 12/2012 |

OTHER PUBLICATIONS

Hsieh et al., "Control algorithms for dynamic attenuators," Med Phys. 41(6): 061907; 2014; 17 pages.
Hsieh et al., "The feasibility of a piecewise-linear dynamic bowtie filter," Med Phys. 40(3):031910; 2013; 12 pages.
Office Action dated Aug. 10, 2015 from U.S. Appl. No. 14/333,459.
International Search Report dated Feb. 1, 2013 from International Application No. PCT/US2012/042469.
Final Office Action from Jan. 11, 2016 from U.S. Appl. No. 14/125,926.
Office Action dated Jan. 14, 2016 from U.S. Appl. No. 14/333,459.

* cited by examiner

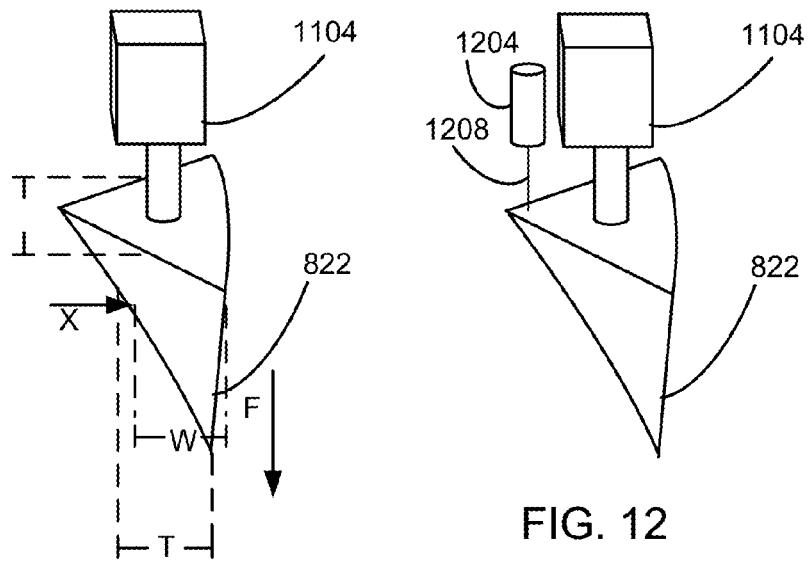
FIG. 11
FIG. 12
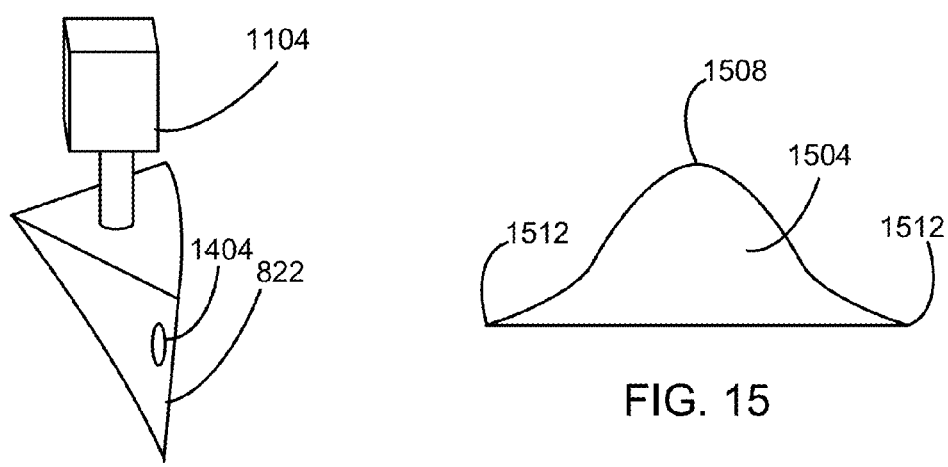
FIG. 14
FIG. 15

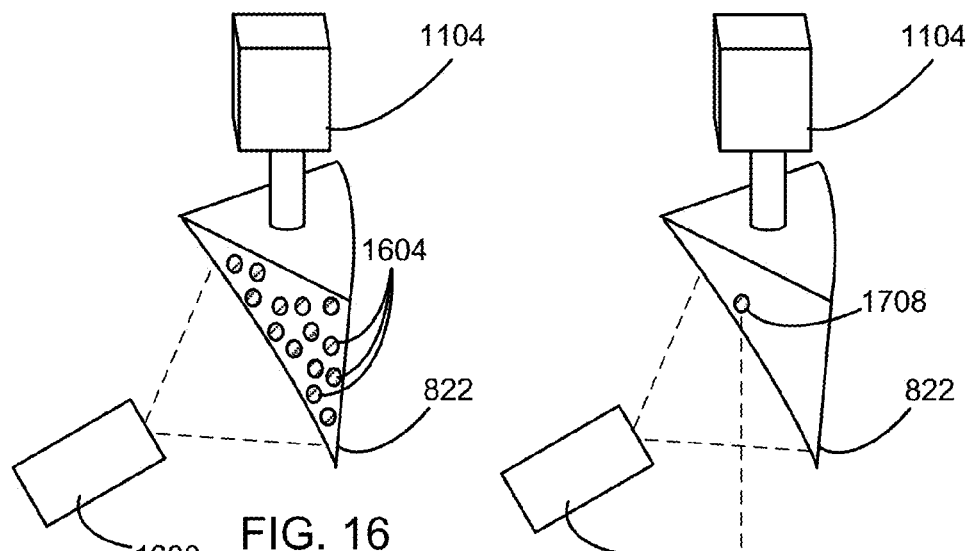
FIG. 16
FIG. 17
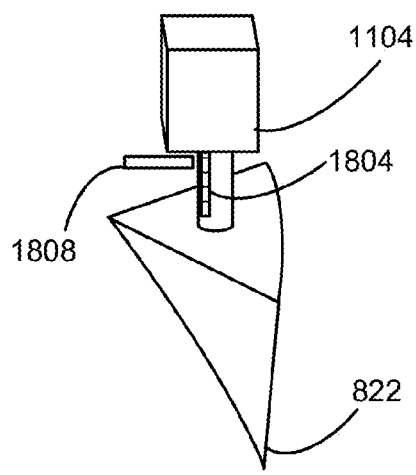
FIG. 18

COMPUTED TOMOGRAPHY SYSTEM WITH DYNAMIC BOWTIE FILTER

CROSS REFERENCE TO RELATED APPLICATIONS

This application is a continuation-in-part under 35 U.S.C. §120 of U.S. patent application Ser. No. 14/125,926, filed on Jun. 14, 2012, entitled COMPUTED TOMOGRAPHY SYSTEM WITH DYNAMIC BOWTIE FILTER, by Pelc et al., which is a National Stage Entry of PCT/US2012/042469 filed on Jun. 14, 2012, entitled COMPUTED TOMOGRAPHY SYSTEM WITH DYNAMIC BOWTIE FILTER, which claims priority to U.S. Provisional Patent Application No. 61/498,175, filed Jun. 17, 2011, entitled SIMULATION OF A DYNAMIC BOWTIE and U.S. Provisional Patent Application No. 61/589,245, filed Jan. 20, 2012, entitled SUPPORTING MATERIAL FOR THE CALIBRATION AND WEDGE DESIGN FOR DYNAMIC BOWTIE. This application further claims priority under 35 U.S.C. §119 from U.S. Provisional Patent Application No. 61/833,719, filed Jun. 11, 2013, entitled COMPUTED TOMOGRAPHY SYSTEM WITH DYNAMIC BOWTIE FILTER, all of which are incorporated herein by reference for all purposes.

GOVERNMENT RIGHTS

This invention was made with Government support under contract EB006837 awarded by the National Institutes of Health. The Government has certain rights in this invention.

STATEMENT OF GOVERNMENT FUNDED RESEARCH

This invention was made with Government support under FA9550-05-C-0059 Awarded by DoD, Air Force Office of Scientific Research, National Defense Science and Engineering Graduate (NDSEG) Fellowship, 32 CFR 168a.

BACKGROUND OF THE INVENTION

This invention relates generally to computed tomography (CT).

SUMMARY OF THE INVENTION

In accordance with the invention, a CT apparatus for scanning an object is provided. An x-ray source is provided, wherein the x-ray source provides a collimated x-ray beam with a cross-section with a length and thickness. A plurality of wedges is provided between the source and object. An actuator is connected to the wedges for moving the wedges substantially perpendicular to the length of the cross-section of the collimated x-ray beam. An x-ray detector is located on an opposite side of the object from the x-ray source and is for detecting x-rays that pass through the object and the plurality of wedges. A gantry rotates the x-ray source, the plurality of wedges, and the x-ray detector around an axis of rotation. A detection system measures the relative position of the plurality of wedges. The detection system comprises an optical sensor and a plurality of optical markers, where each wedge has at least one optical marker attached.

In another manifestation of the invention, a CT apparatus for scanning an object is provided. An x-ray source is provided, wherein the x-ray source provides a collimated x-ray beam with a cross-section with a length and thickness. A plurality of wedges is provided between the source and object. An actuator is connected to the wedges for moving the wedges substantially perpendicular to the length of the cross-section of the collimated x-ray beam. An x-ray detector is located on an opposite side of the object from the x-ray source and is for detecting x-rays that pass through the object and the plurality of wedges. A gantry rotates the x-ray source, the plurality of wedges, and the x-ray detector around an axis of rotation. A detection system measures the relative position of the plurality of wedges. The detection system comprise an optical sensor and a laser, which generates a laser light, which illuminates a portion of a wedge, where when the wedge is moved in the direction of movement, the portion of the wedge illuminated by the laser light moves in a direction different than the direction of movement.

In another manifestation of the invention, a CT apparatus for scanning an object is provided. An x-ray source is provided, wherein the x-ray source provides a collimated x-ray beam with a cross-section with a length and thickness. A plurality of wedges is provided between the source and object. An actuator is connected to the wedges for moving the wedges substantially perpendicular to the length of the cross-section of the collimated x-ray beam. An x-ray detector is located on an opposite side of the object from the x-ray source and is for detecting x-rays that pass through the object and the plurality of wedges. A gantry rotates the x-ray source, the plurality of wedges, and the x-ray detector around an axis of rotation. A detection system measures the relative position of the plurality of wedges. The detection system comprises a magnetic sensor system and a plurality of magnetic markers, where each wedge has at least one magnetic marker.

The invention and objects and features thereof will be more readily apparent from the following detailed description and appended claims when taken with the drawings.

BRIEF DESCRIPTION OF THE DRAWINGS

FIG. 11 is a schematic perspective view of a wedge attached to an actuator.

FIG. 12 schematic perspective view of a wedge and actuator with an optical system.

FIG. 14 is a schematic view of a wedge with an actuator and a high contrast marker.

FIG. 15 is a top view of a wedge that has a more Gaussian shape.

FIG. 16 is a schematic view of a wedge with an actuator used in another embodiment.

FIG. 17 is a schematic view of a wedge with an actuator used in another embodiment.

FIG. 18 is a schematic view of a wedge with an actuator used in another embodiment.

DETAILED DESCRIPTION OF ILLUSTRATED EMBODIMENTS

Figure 1:
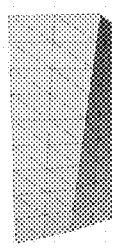
FIG. 1 shows three-dimensional renderings for a single wedge.

The bowtie filter in CT customizes the flux profile of the incident x-ray beam based on its fan angle. Traditionally, static bowtie filters are tailored only for very generic scans (e.g., head or body) and for the average patient. An embodiment of the invention provides a dynamic bowtie, which can present a time-dependent piecewise-linear attenuation profile in fan angle. This dynamic bowtie presents several advantages over traditional bowtie. An embodiment of the invention reduces the dynamic range on the detector. Using clinical datasets, we found that the dynamic range may be reduced by a factor of fifty in most parts of the body and by a factor of four in the most challenging regions. Such a reduction in dynamic range may be particularly welcome in applications involving photon-counting detectors. The radiation dose delivered remains comparable to the traditional bowtie, and the noise distribution of the image is made more uniform. Beam hardening artifacts resulting from the dynamic bowtie were analyzed and suppressed with a two-pass algorithm. Other potential advantages of the dynamic bowtie are provided, and include lower radiation dose to the patient and/or improved image quality.

It is often desirable to measure the different line integrals that CT measures with differing number of photons. Those line integrals that pass through clinically relevant regions or through highly attenuating tissue should be measured with more photons; conversely, rays that have little attenuation or which go through irrelevant or radiation sensitive tissue should be measured with fewer photons. Dose concerns aside, extra photons delivered to the wrong location may even degrade image quality if they contribute to excess scatter, or if a photon-counting detector (PCXD) is employed and count rate loss ensues. Ideally, it would be possible to take each ray in a sinogram and choose, on a ray-by-ray basis, how many photons are used to measure that line integral. Currently employed technologies provide us with comparatively limited ability to control flux.

The traditional bowtie filter is a pre-patient attenuator which attenuates photons as they leave the x-ray source and before they reach the patient, but with a static attenuation profile that does not vary in time. In other words, the bowtie filter provides a constant attenuation profile that is a function of fan angle but is constant for an entire volumetric scan. The bowtie filter is usually designed to compensate for the varying path length through the patient and helps to equalize the radiation incident on the detector, reducing the dynamic range on the detector. In reducing the dynamic range, the bowtie also reduces the scatter, which can be dominated by lightly attenuating regions. The radiation dose is also alleviated because the bowtie filter tends to selectively remove photons in regions where the noise statistics are already very good and for which additional photons would produce very little incremental benefit. One limitation of the bowtie filter is that the attenuation profile it produces is fixed and cannot change with time.

Tube current modulation is another technology which can control flux and is complementary to the bowtie filter in that it can modulate the photon flux as a function of time, but not of fan angle. Tube current modulation has the additional advantage of being quite flexible, and can be customized on a per-patient basis; the bowtie filter, in contrast, must be designed for a generic scan on a generic patient. Tube current modulation does not change the scatter to primary ratio, but can reduce the dynamic range and significantly improve dose efficiency. Together, the bowtie filter and tube current modulation give some control over the flux in both time and fan angle, but still leave room for improvement.

An embodiment of the invention provides a dynamic bowtie filter that is directed towards the goal of improved control of the x-ray flux. The embodiment is able to provide an attenuation profile that is piecewise linear in fan angle, and is able to dynamically morph as the gantry rotates. Previous dynamic bowtie designs have been reported in the patent literature, but they typically consist of only two or three moving parts and are often optimized for elliptical water cylinders. Such designs do not afford the level of flexibility of a piecewise-linear attenuation profile.

This extra flexibility would be especially beneficial for enabling photon-counting detectors, which currently suffer from inability to handle high count rates. When the incident flux is low compared to the count rate limitation, these detectors provide superior detective quantum efficiency (DQE) and intrinsic energy discriminating capabilities. As the incident flux increases, however, count rate loss and pulse pile-up occur, which damages the DQE and the energy information. The reduction in the dynamic range provided by a dynamic bowtie could be used to attenuate the rays where count rate loss and pulse pile-up are most significant, making photon-counting CT with detectors with relatively modest count rate limitation feasible. Besides its application to photon-counting detectors, a dynamic bowtie filter may provide superior scatter reduction, may be useful for reducing the dose of a scan without sacrificing diagnostic quality, and could additionally enable region-of-interest scans.

Design

An embodiment of the invention provides an attenuation profile that is piecewise linear in fan angle. Mathematically, a piecewise linear function can be achieved by using a basis set of triangle functions, regularly spaced in fan angle and with variable height. To be concrete, let us define $\Lambda(x)$ to be a triangle function, so that $\Lambda(x)=\max(0,1-|x|)$. Now we introduce $f(x)$ defined as $$f(x) = \sum_{k=-\infty}^{\infty} c_k \Lambda\left(x - \frac{k}{2}\right)$$

This function can be set to become any piecewise linear function we desire (with piece length unity) by changing $c_k$.

In two dimensions, this mathematical notion can be translated into practice by taking advantage of the flexibility afforded via the third dimension. We use the fact that most multi-slice scanners have small beam thickness in the z-direction, and for now make the approximation that we are only looking at a single slice. Each triangle function $c_k\Lambda(x)$ can then be implemented using wedges of attenuating material whose cross-section is a triangle of a given size base but where the height of the triangle depends on position along the length of the wedge. The height of the wedge determines the width or thickness of material traversed by the x-ray beam. Any axial slice through the wedge would present a triangle function attenuation profile. By moving or scrolling the wedges up and down in the third dimension, we would scale the height of the triangle function presented. FIG. 1 shows three-dimensional renderings for a single wedge. Different axial slices present triangular-shaped attenuation profiles of different height. Moving the wedge up and down scales the height.

Figure 2A:
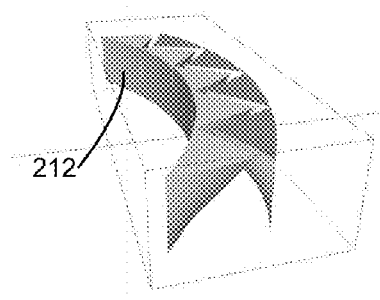
FIG. 2A shows a perspective view of an embodiment of the invention that uses two rows of wedges to form a dynamic bow tie.
Figure 2B:
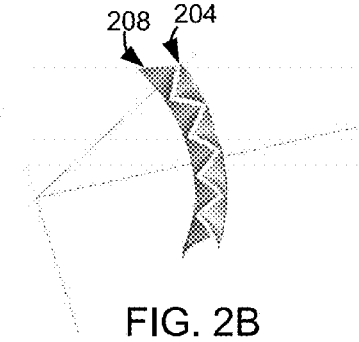
FIG. 2B shows a top view of the two rows forming the dynamic bow tie.

Building up the entire piecewise linear function $f(x)$ requires multiple overlapping triangular elements. The wedges cannot physically overlap, but the multiple triangular wedges can be grouped into two separate layers, one offset from the other by half of the triangle base. An x-ray beam would pass through both layers, and together would be attenuated by the piecewise linear function of the embodiment. FIG. 2A shows a perspective view of an embodiment of the invention that uses two rows of wedges to form a dynamic bowtie. FIG. 2B shows a top view of the two rows forming the dynamic bowtie. By moving each wedge separately we are able to build up the piecewise linear attenuation profile that we desire. In a fan beam CT scanner this assembly would be curved as part of a circle, and the x-ray source would be placed at the center of that circle. Other embodiments may have more than two rows of wedges.

In an embodiment of the invention, a dynamic bowtie would be placed a short distance away from the x-ray tube. This embodiment has the bowtie parameters found in the table below.

| | |
|---|---|
| Source-isocenter distance | 50 cm |
| Detector-isocenter distance | 50 cm |
| Source-bowtie distance | 8 cm |
| Number of triangular wedges | 15 |
| Width of each triangle | 11.4 mm |
| Material | Iron |
| Maximum depth of wedge | 6.1 mm |
| Axial height extent of wedge | 40 mm |
| Axial FOV of scan | 4 cm |
| Actuator speed | 25 cm/sec |

The choice of material is dependent on beam-hardening characteristics. The choice of material also changes the maximum height of the wedges which may be important from a manufacturing and space perspective.

Most multi-slice scanners capture several centimeters of data in z in a single scan. The bowtie, as presented, will produce an attenuation profile that is linear in z. This can be corrected for with the use of a slanted compensator, which has a constant thickness in fan angle but is slanted in z to counteract the effect of the existing slant. Together, the bowtie filter plus the compensator will produce an overall attenuation that is constant in z. This is acceptable for most current CT systems because a typical CT system today has an in-plane field of view that is much longer than its axial field of view. Other variations on this design may allow variation of attenuation in the z direction. Depending on the goals of the scan, the compensator may not be necessary; or, portions of the compensator may be withdrawn in order to increase the flux in some parts of the x-ray fan beam. Likewise, some of the wedges may be withdrawn from the beam so as to allow maximum flux to penetrate the object.

It would is simple to extend the concept of the present invention to other basis functions besides triangles and thereby build up more general splines in other embodiments of the invention. The extension to other basis functions could include, as one example, smoothed triangle functions, which would create an attenuation function that is even smoother than piecewise linear and may produce fewer artifacts.

From a physical standpoint, the parameters in Table 1 were chosen so the dynamic bowtie filter in the embodiment of the invention can be immediately actionable. The wedges in this embodiment are relatively easy to manufacture and work with, and would provide the ability to attenuate a typical CT x-ray beam by up to three orders of magnitude. If it were more convenient to make the bowtie smaller or larger, the choice of wedge material would simply change. The speed of the motors which are used to scroll the wedges are another design consideration, and they should be chosen in conjunction with the angle of the wedge; together, these parameters determine the speed at which the dynamic bowtie is able to morph with time. Larger angles permit a more agile piecewise linear attenuation profile, but they introduce more variation in the z-direction. A dynamic bowtie employing more actuators and faster motors would obviously provide superior dynamic ability, but other embodiments are simpler to build.

Calibration of the dynamic bowtie is challenging but desirable and possible. It is not important to have extremely precise control over the position of each wedge in the bowtie, but it is imperative that the position of the wedges be known. The conversion of the measured intensity to a line integral of attenuation needs knowledge of the incident intensity, and this is affected by the wedge positions. The beam hardening correction also needs to be adjusted on a per-ray basis using the known wedge profiles in a manner than is known in the art, for example as described below. Based on these facts and the parameters listed in the table, the dynamic bowtie is quite actionable and practical with today's technology.

Methods

In a simulation of an embodiment of the invention, we sought to quantify the ability of the embodiment of the invention, especially with interest in the performance of the bowtie in more difficult settings, such as a thorax cross-section with sharp transitions. Besides the thorax, we also simulated the performance of the dynamic bowtie in the abdomen and in the shoulders. All simulations were conducted in two dimensions and we ignore volumetric effects. In this simulation the photons were assumed to be monoenergetic at 60 keV. We did not model imperfections relating to the implementation of the dynamic bowtie, but assumed that we had direct access to the piecewise-linear attenuation profile that the embodiment of the invention should be able to furnish for us, subject only to the finite motor speed of the bowtie. All tests were compared to a reference bowtie similar to the body bowtie in a GE CT scanner.

The most basic task of the bowtie is to reduce the dynamic range on the detector. The dynamic range is defined as the largest possible ratio of photons arriving at any two measurements on the sinogram. The dynamic range with the traditional bowtie can be calculated simply by looking at the sinogram, by finding the ratio of the number of photons arriving at the least and most attenuated pixel in the sinogram.

To calculate the dynamic range with the dynamic bowtie, it was necessary to first determine the trajectories of the different wedges of the dynamic bowtie over time. To do this, we assumed that a pilot CT scan was available and solved an optimization problem whose objective was to minimize the dynamic range. For the purpose of this simulation, we assumed that the pilot CT scan was noiseless, although the addition of noise is not expected to change the results.

Minimizing the dynamic range was cast as a convex optimization problem so that the best trajectories could be calculated using the CVX convex optimization package with a guarantee on optimality. The object attenuation was measured by the pilot scan. The added bowtie attenuation on the other hand, was modeled by breaking up the bowtie into the component wedges in separate views. With M bowtie wedges and N views, the added bowtie attenuation was calculated as a linear combination of MN different images. To be precise, let $\theta$ the continuous fan angle and $v$ be the discrete view number. Then we can define $$\mu_{tot}(\theta,v)=\mu_{object}(\theta,v)+\mu_{added}(\theta,v)$$

$$\mu_{added}(\theta,v)=\Sigma x_{ij}\Lambda(\theta-i)\delta(v-j)$$

The optimization problem was cast into the convex formulation

| Minimize | $\max(\mu_{tot}(\theta, v)) - \min(\mu_{tot}(\theta, v)) + \epsilon \Sigma x^2_{ij}$ |
|---|---|
| Subject to | $\|x_{ij} - x_{(i+1)j}\| < s_{max}$ for $i = 1, 2 \ldots M - 1$ |
| | $0 \leq x_{ij} \leq x_{max}$ |

Here, $\epsilon\Sigma x_{ij}^2$ is a regularization term with $\epsilon$ being a small positive constant. As defined, the dynamic range is unaffected by uniform shifts in attenuation, but adding on extra attenuation is undesired from a flux standpoint. $S_{max}$ is a constant which determines the highest speed by which the triangle functions can grow or shrink in time, and is set by the speeds of the motors and similar constraints.

In order to decrease the computational complexity, we ran the optimization problem on a downsampled sinogram with fewer views and angular samples. However, the optimal solution in the downsampled sinogram is expected to be quite good on the full sized version of the sinogram, as well.

As a reference, we compared the dynamic bowtie to a static bowtie. The bowtie used by the reference system is the GE body bowtie.

With the tube current modulation profile and the trajectories of the dynamic bowtie in hand, it was possible to determine both the radiation dose delivered and the noise statistics of the resulting scan. The variance of each pixel in the reconstruction was produced by adding the variance of each individual ray that is backprojected to a given pixel, scaled by a constant that depends on the deapodization kernel used. The variance of each ray, in turn, was found by assuming simple Poisson statistics at the detector.

The radiation dose was found using Monte Carlo simulations with the GEANT4 software package. To simplify the calculations, the original DICOM image was downsampled by a factor of four so that the simulations were run using only 128×128 pixels instead of the original 512×512 pixels. The two-dimensional picture was extruded by twenty centimeters in the third dimension in order to obtain an estimate of the dose contribution of photons that undergo Compton scattering. The bowtie itself was modeled as being purely attenuating, and photons that undergo Compton scattering from the bowtie itself are ignored. In interpreting the DICOM images, pixels less than −700 HU were regarded as air. Pixels between −700 and 200 HU were regarded as being composed of water of the density that would produce the observed HU value. Pixels above 200 HU were regarded as being a linear combination of cortical bone and water by volume, with the linear weights determined by the need to produce the observed HU value.

Beam Hardening Simulations

Using the same actuator trajectories previously obtained, a polychromatic (120 kVp) simulation of the bowtie was conducted to check that the beam hardening artifacts remained acceptable. The clinical data was segmented into air, cortical bone, and water. The images were then reconstructed in three ways: without any beam hardening corrections, with a beam hardening correction, and with a two-pass beam hardening correction. In order to more cleanly capture the effects of the beam hardening correction, we did not model the tissue as being mixtures of air, water and bone, but rather, segmented them in a hard, ternary fashion. This allowed the effects of beam hardening to be more clearly seen without any anatomical background. The beam hardening artifacts induced by the virtual bowtie were compared with those coming from a standard, static bowtie.

The two-pass beam hardening correction scheme was based on published two-pass algorithms. Briefly, in the first pass of the algorithm, the incident photon count was used in conjunction with the depth and material of the bowtie penetrated to estimate the equivalent water length. We applied filtered background proection (FBP) to this data to get a first pass image, which we then segmented into mixtures of water, bone, and air depending on CT number. In the second pass, we applied a forward projection step and estimated how much bone and water each ray would have passed through, and we used these numbers to estimate the magnitude of the error that was made in the first pass. The result was then applied as a correction term.

Results

Figure 3A:
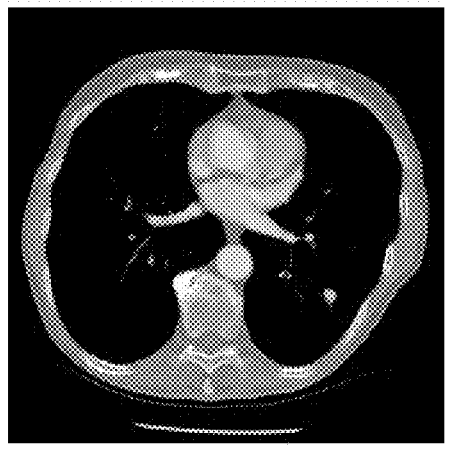
FIG. 3A is a starting DICOM image of a thorax for simulation.
Figure 3B:
FIG. 3B is a starting DICOM image of an abdomen for simulation.
Figure 3C:
FIG. 3C is a starting DICOM image of shoulders for simulation.

A system of 17 actuators was assumed to produce the following images. FIGS. 3A-C show the three datasets that were used. FIG. 3A is a starting DICOM image of a thorax for simulation. FIG. 3B is a starting DICOM image of an abdomen for simulation. FIG. 3C is a starting DICOM image of shoulders for simulation.

Dynamic Range

Figure 4A:
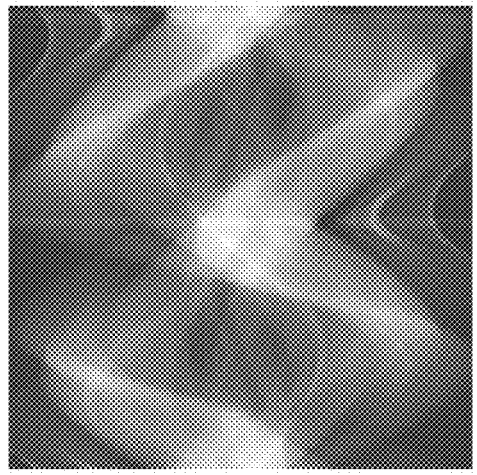
FIGS. 4A-F show an attenuation sinogram of shoulders, thorax, and abdomen.
Figure 4B:
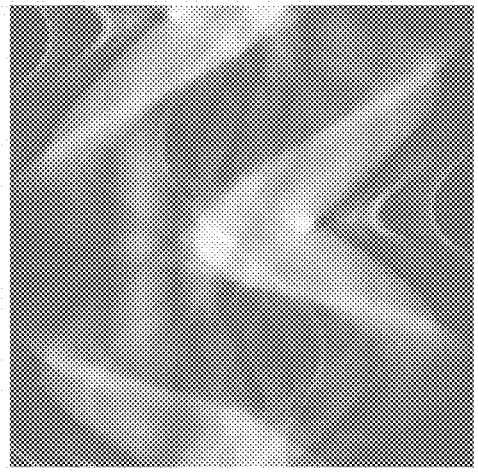
Figure 4C:
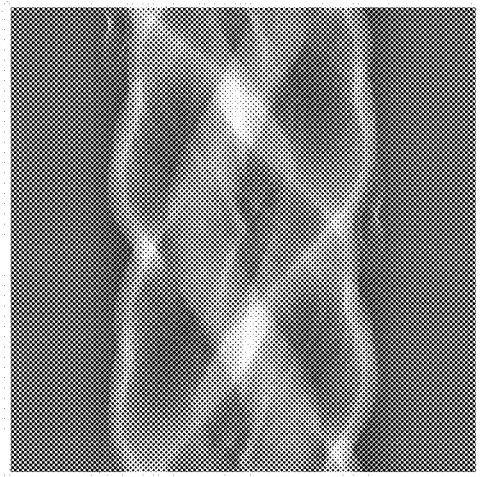
Figure 4D:
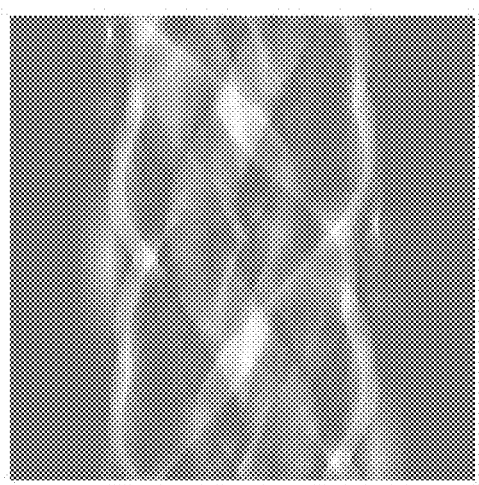
Figure 4E:
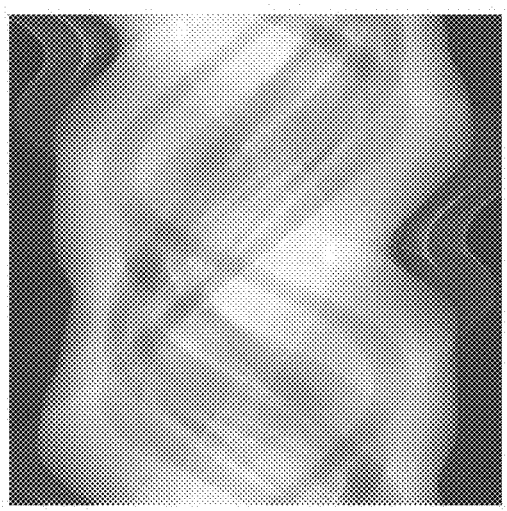
Figure 4F:
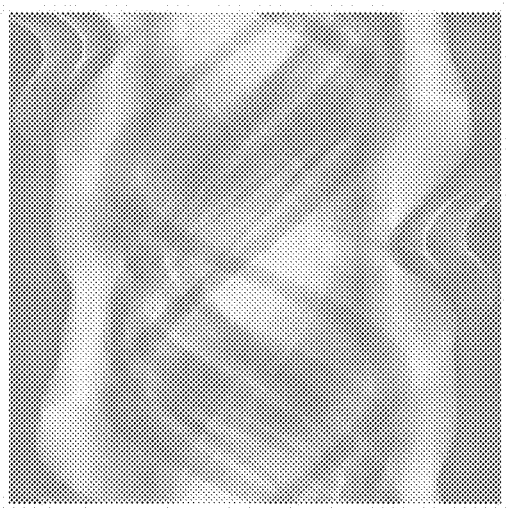

The dynamic range decreased by factors of four to fifty depending on the dataset used. FIGS. 4A-F show an attenuation sinogram of shoulders (FIGS. 4A-B), thorax (FIGS. 4C-D), and abdomen (FIGS. 4E-F). Results from the static bowtie are shown in FIGS. 4A, C, and E, and results from the dynamic bowtie are shown in FIGS. 4B, D, and F. The sinograms for the same dataset are shown at the same windowing. The dynamic range for the reference bowtie and for the embodiment of the dynamic bowtie is shown below.

| Dataset | Reference Bowtie Dynamic Range | Dynamic Bowtie Dynamic Range | Ratio |
|---|---|---|---|
| Adult thorax | 53 | 17 | 3.2x |
| Adult shoulder | 1577 | 133 | 11.9x |
| Adult abdomen | 381 | 14 | 27.1x |

Figure 5A:
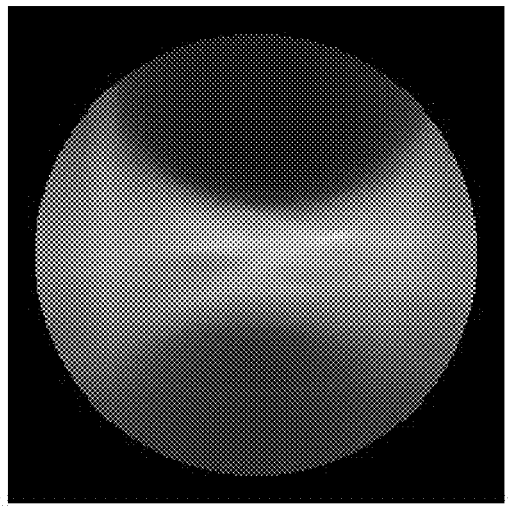
FIGS. 5A-F show the noise distribution, scaled by arbitrary reference noise of shoulders, thorax, and abdomen.
Figure 5B:
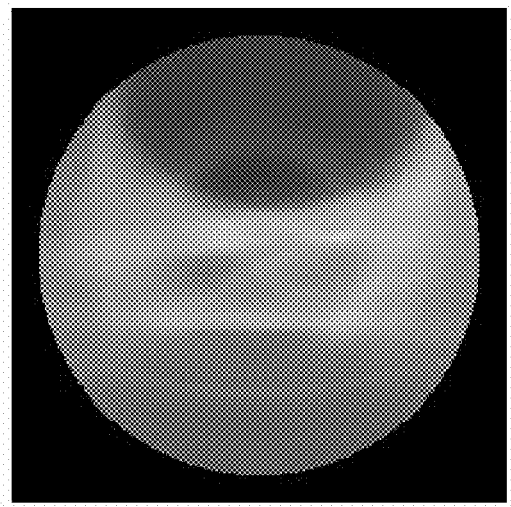
Figure 5C:
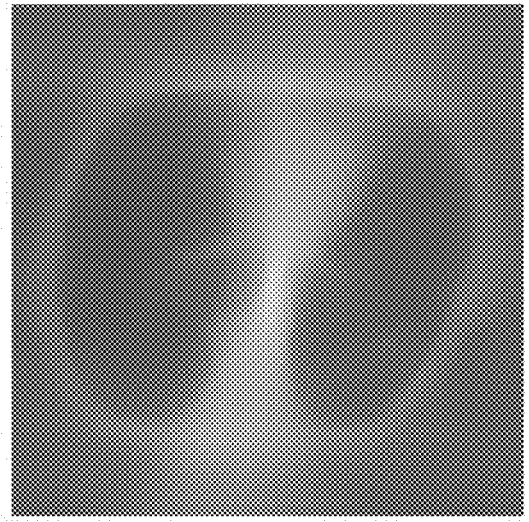
Figure 5D:
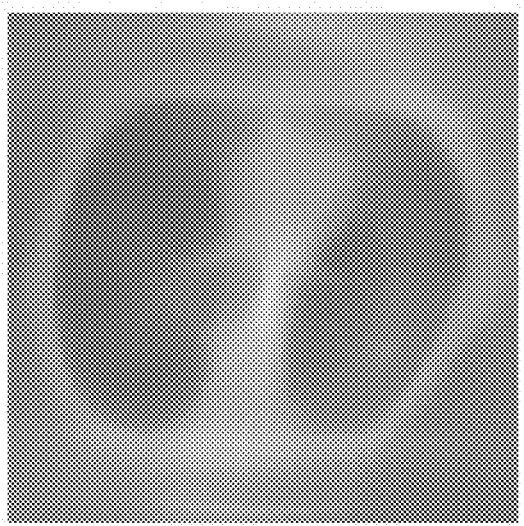
Figure 5E:
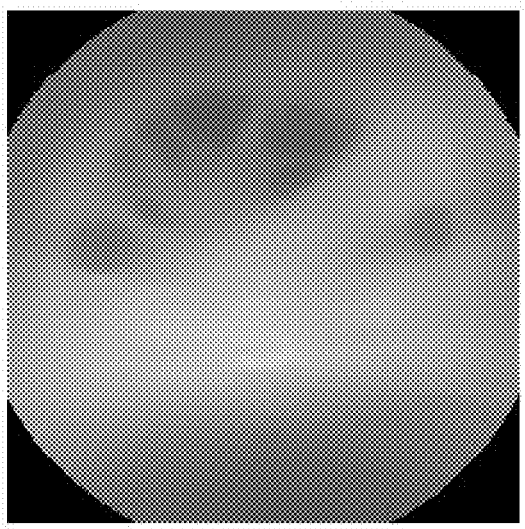
Figure 5F:
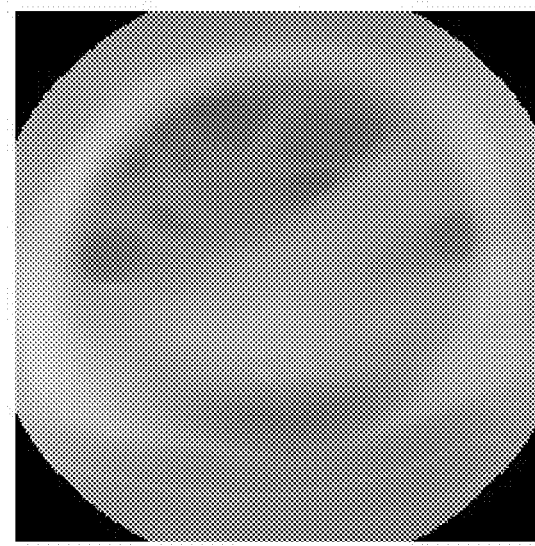

FIGS. 5A-F show the noise distribution, scaled by arbitrary reference noise of shoulders (FIGS. 5A-B), thorax (FIGS. 5C-D), and abdomen (FIGS. 5E-F). The noise distribution is reported as standard deviation of pixel value and not a variance. FIGS. 5A, C, and E show the scaled noise distribution for a reference bowtie. FIGS. 5B, D, and F show scaled noise distribution for a dynamic bowtie.

Figure 6A:
FIGS. 6A-F show the dose distribution as calculated from Monte Carlo simulation.
Figure 6B:
Figure 6C:
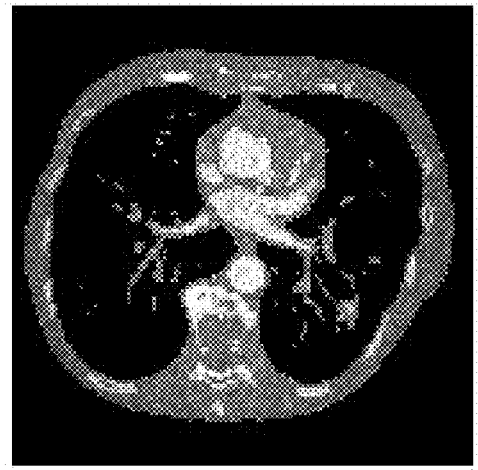
Figure 6D:
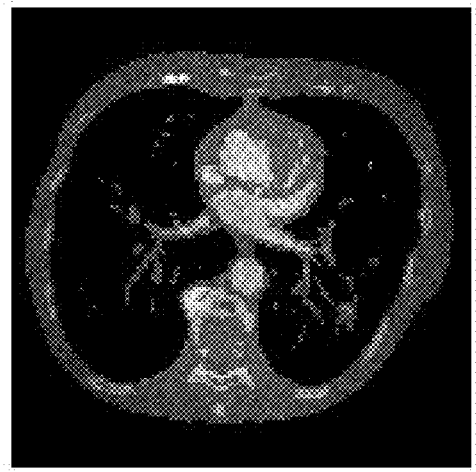
Figure 6E:
Figure 6F:
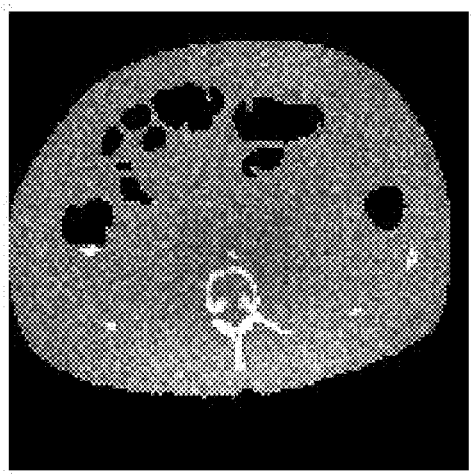

FIGS. 6A-F show the dose distribution as calculated from Monte Carlo simulation. FIGS. 6A, C, and E are simulations that result from a dynamic bowtie. FIGS. 6B, D, and F are simulations that result from using a static bowtie filter.

A marked decrease in dose can be observed in some datasets, e.g. in the shoulder (FIG. 6A-B). If desired, the optimization objective could have been set to minimize a noise metric such as peak or average variance for a fixed level of dose.

Beam Hardening Simulations

Figure 7A:
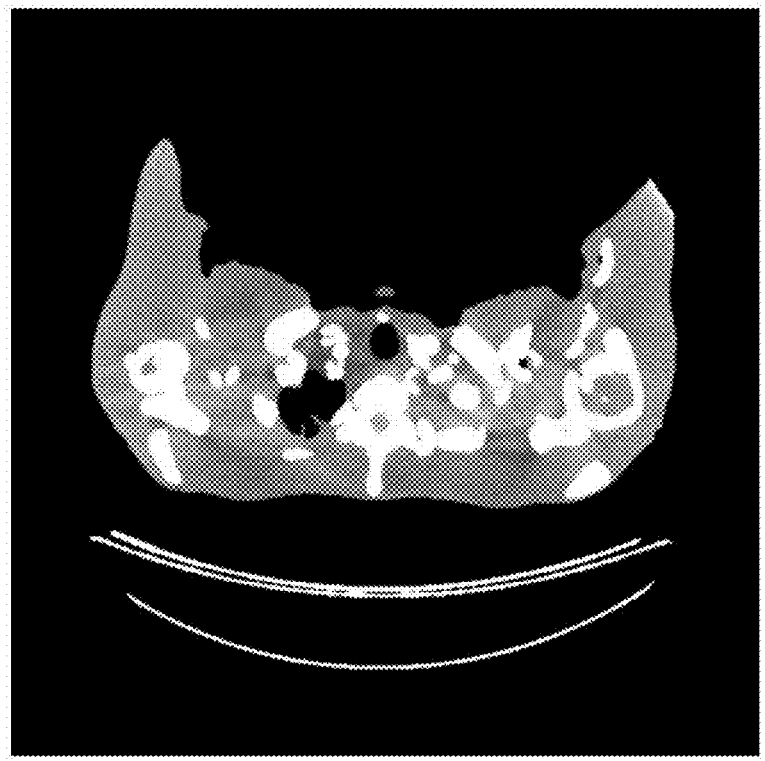
FIG. 7A shows the result of a hardening correction using a single pass algorithm.
Figure 7B:
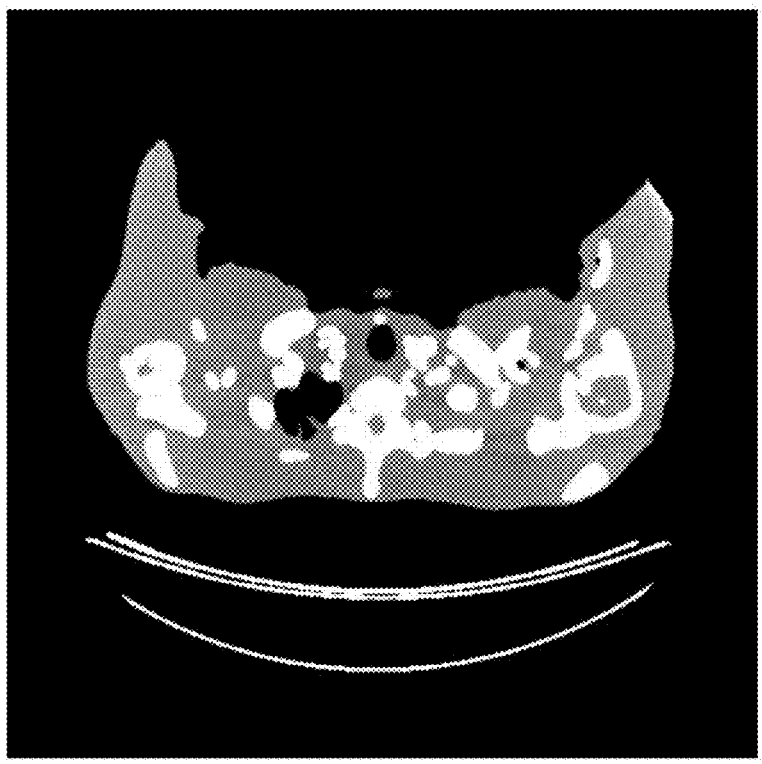
FIG. 7B shows the result of a hardening correction using a two-pass algorithm.

A simple shoulder phantom was segmented in a hard ternary fashion into cortical bone, water, and air. The initial reconstruction with only a one-pass correction resulted in some residual beam hardening artifacts. The one-pass correction is a water beam hardening correction that is channel and view-dependent, compensating for the different lengths of bowtie attenuation. A two-pass algorithm was effectively able to clean it up. FIG. 7A shows the result of a hardening correction using a single pass algorithm. FIG. 7B shows the result of a hardening correction using a two-pass algorithm. The artifact level of each was comparable to the counterpart standard bowtie image.

The two-pass algorithm first applies the original one-pass correction, which is a view and channel dependent water beam hardening correction. Then, the amount of bone present in each ray is estimated by segmentation and forward projection. This amount of bone is used to estimate the error present in the water beam hardening correction, and the estimated error is then subtracted from the image.

Based on the mathematical starting point of producing piecewise linear functions using triangle functions, an embodiment of the invention provides a dynamic bowtie that can be implemented using wedges, with different axial slices of the wedge resulting in triangles of different heights. This dynamic bowtie design remains quite practical and actionable.

In simulations, the dynamic bowtie was able to reduce the dynamic range by factors from between 4 to 50 depending on the part of the body studied. These results suggest that the possibility of using this dynamic bowtie in conjunction with photon-counting detectors of relatively modest count rates. The dynamic bowtie could also be applied to other objectives, such as noise or dose reduction. The thorax image was challenging because of the sharp transitions between the lungs and the tissue surrounding the lungs, but reasonably good results were still obtained, and here the dynamic bowtie had the fringe benefit of reducing the radiation dose delivered without increasing the maximum noise of the image. In the shoulders and in the abdomen, the dynamic range was reduced by over an order of magnitude. The beam hardening artifacts of the dynamic bowtie were also studied, and preliminary results suggest that while they are somewhat different from traditional beam hardening artifacts, they can be corrected with a two-pass algorithm.

Examples

Figure 8:
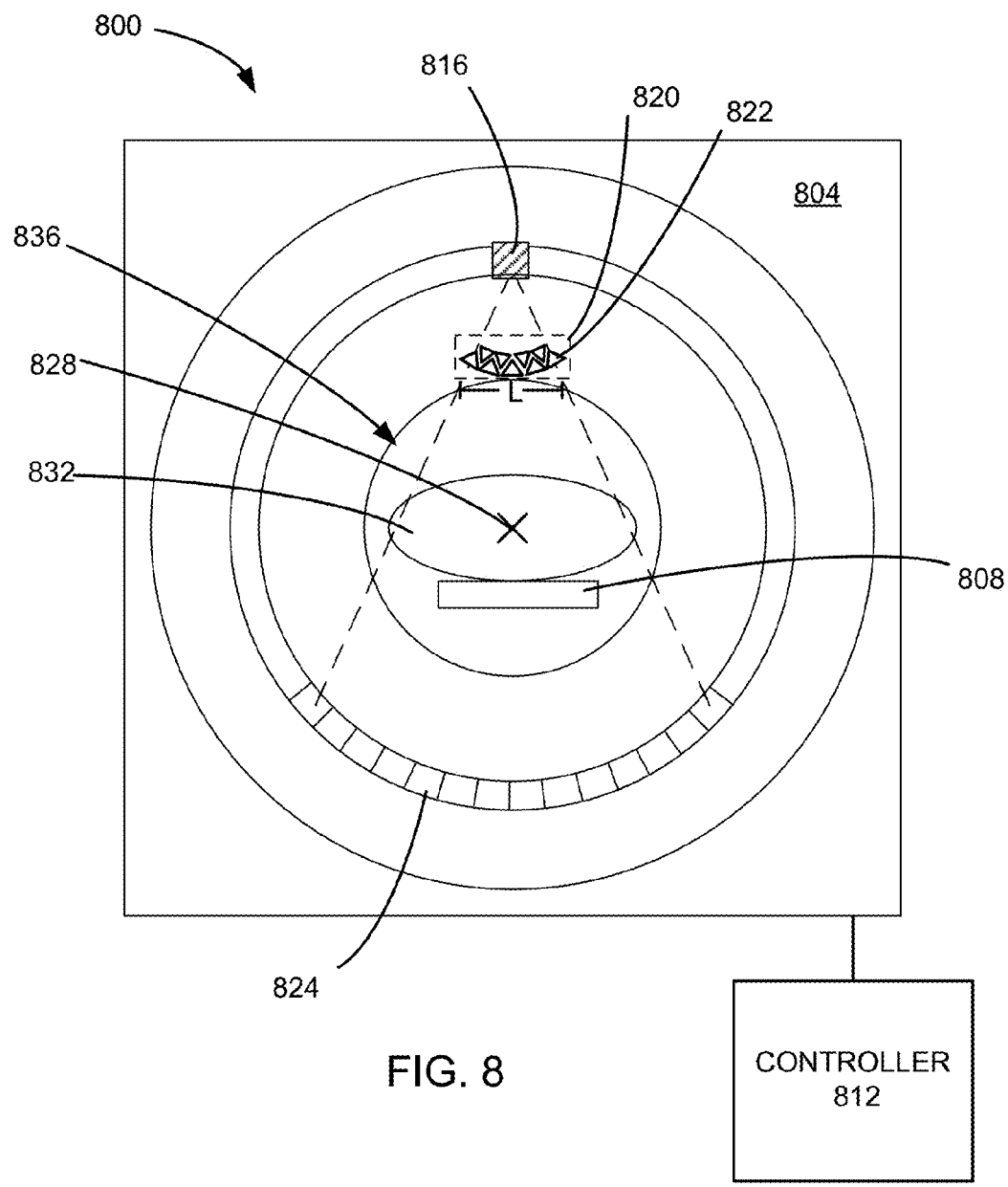
FIG. 8 is a schematic end view of an x-ray CT system that may be used in an embodiment of the invention.

To facilitate understanding of the invention, FIG. 8 is a schematic end view of an x-ray CT system 800 that may be used in an embodiment of the invention. The CT system comprises a gantry 804, a support 808, a dynamic bowtie filter 820, and a controller 812. The dynamic bowtie filter 820 is like the dynamic bowtie filter shown in FIG. 2A and FIG. 2B and comprises a plurality of wedges 822. The gantry supports an x-ray source 816, a dynamic bowtie filter 820, and an x-ray detector 824. The gantry 804 rotates the x-ray source 816, dynamic bowtie filter 820, and x-ray detector 824 around an axis of rotation 828 that extends into the page. The support 808 supports an object 832 to be scanned. The support 808 or gantry 804 translates the object 832 with respect to the x-ray source 816, dynamic bowtie filter 820, and x-ray detector 824 along the axis of rotation 828 through an aperture 836 in the gantry 804. In this embodiment, the x-ray source 816 provides a collimated beam that has a cross-section with a length (L) and thickness. The axis of rotation 828 is substantially perpendicular to the length of the cross-section of the collimated beam.

The dynamic bowtie filter 820 is shown in FIG. 8 and also in FIGS. 2A and 2B. It can be seen that along the direction of the length L of the cross-section of the x-ray beam the thicknesses of the wedges 822 change. More specifically, since the wedges are triangular, the thicknesses of the wedges increase and then decrease or alternately increase and decrease along the direction of the length L of the cross-section. In this embodiment, the wedges are provided in a first row 204 and a second row 208, as shown in FIG. 2B. The wedges in the second row are placed to overlap with wedges in the first row, so that thicker parts of the wedges in the second row line up with the junctions between wedges in the first row and thicker parts of the wedges in the first row line up with the junctions between wedges in the second row along the direction between the x-ray source and the object. In this embodiment, the backsides 212 of the wedges forms a curved rectangular surface, as shown in FIG. 2A.

Figure 9:
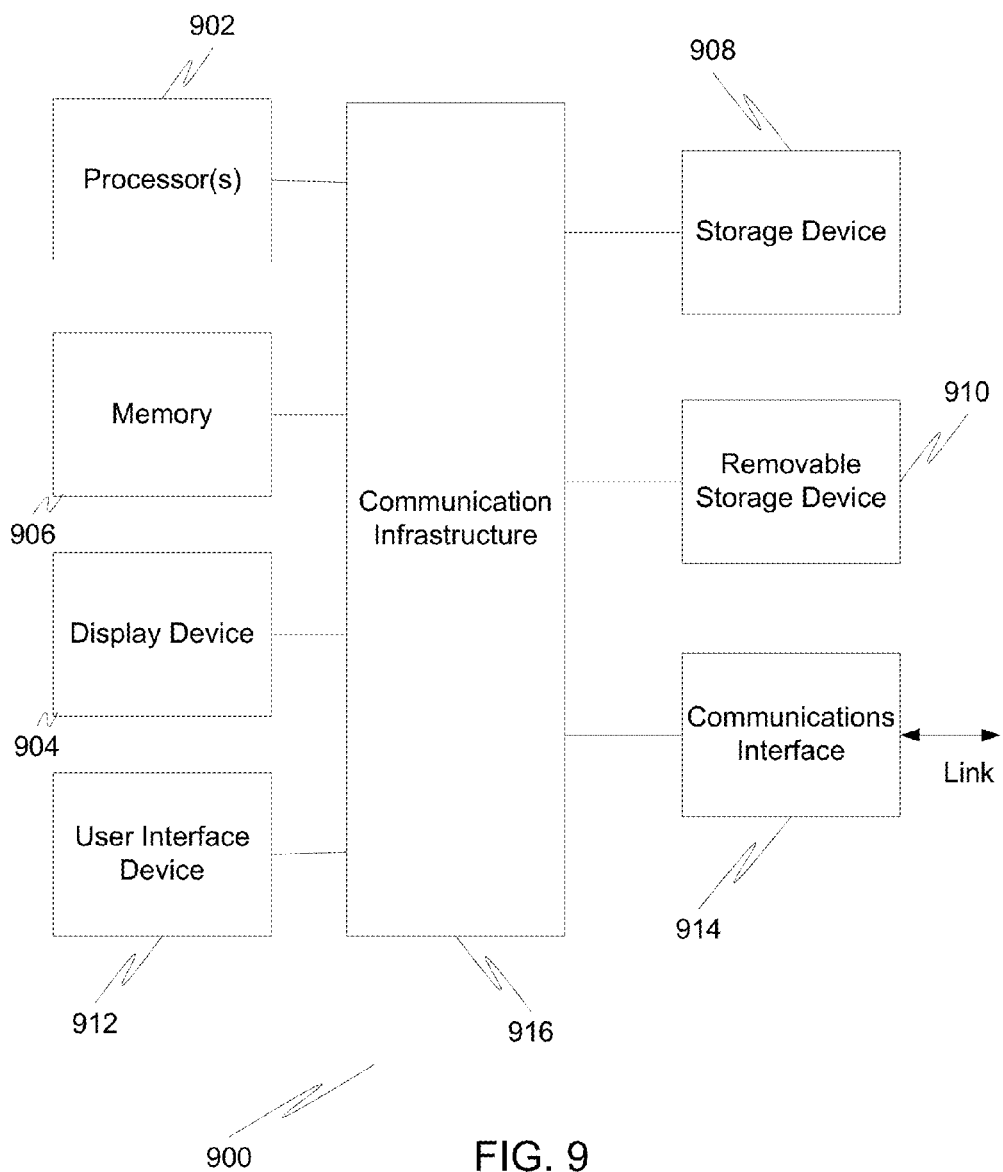
FIG. 9 is a high level block diagram showing a computer system, which is suitable for implementing a controller used in embodiments of the present invention.

FIG. 9 is a high level block diagram showing a computer system 900, which is suitable for implementing a controller 812 used in embodiments of the present invention. The computer system may have many physical forms ranging from an integrated circuit, a printed circuit board, and a small hand-held device up to a huge super computer. The computer system 900 includes one or more processors 902, and further can include an electronic display device 904 (for displaying graphics, text, and other data), a main memory 906 (e.g., random access memory (RAM)), storage device 908 (e.g., hard disk drive), removable storage device 910 (e.g., optical disk drive), user interface devices 912 (e.g., keyboards, touch screens, keypads, mice or other pointing devices, etc.), and a communication interface 914 (e.g., wireless network interface). The communication interface 914 allows software and data to be transferred between the computer system 900 and external devices via a link. The system may also include a communications infrastructure 916 (e.g., a communications bus, cross-over bar, or network) to which the aforementioned devices/modules are connected.

Figure 10:
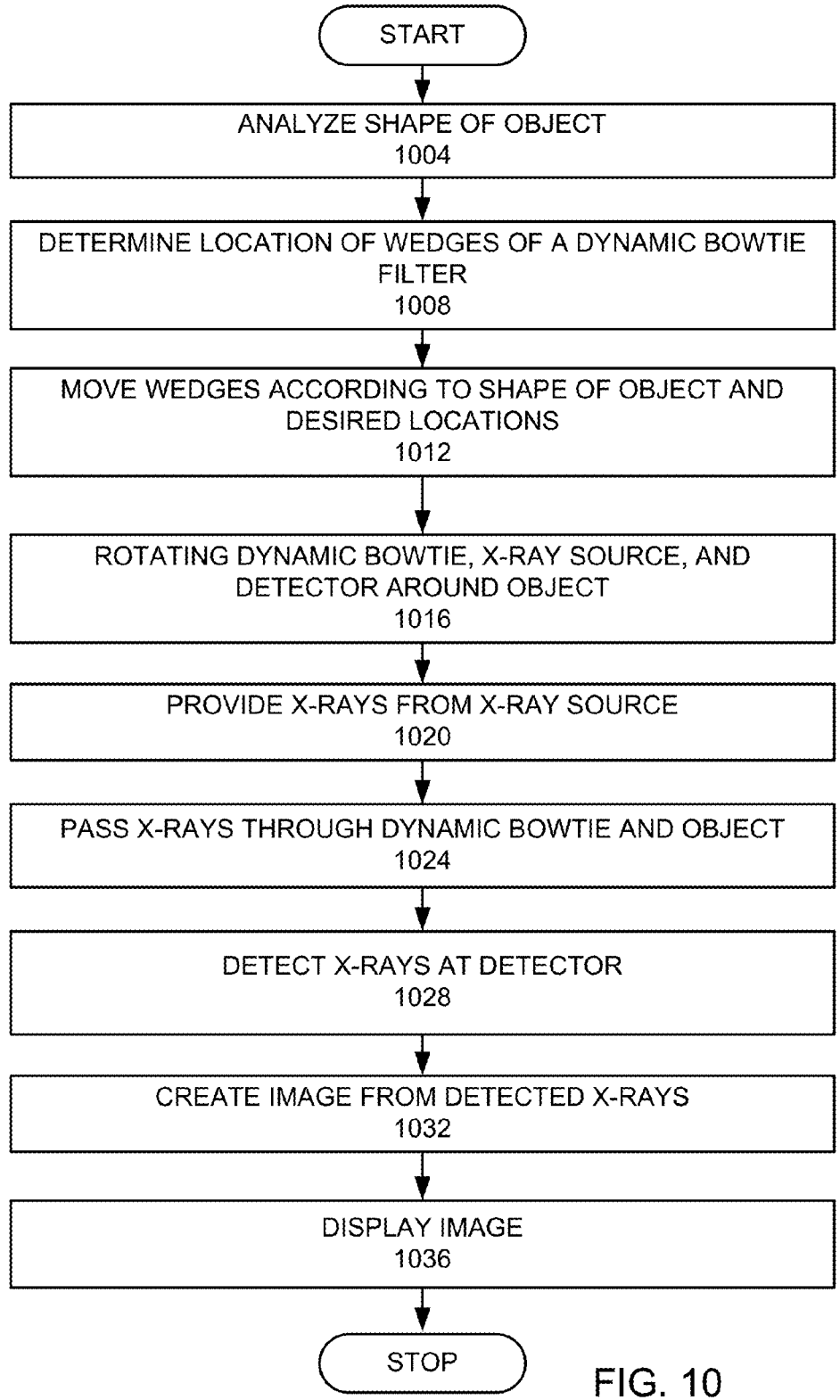
FIG. 10 is a high level flow chart of an embodiment of the invention.

To facilitate the understanding of the invention, FIG. 10 is a high level flow chart of an embodiment of the invention. An object 832 is placed on the support 808, which translates the object along the axis of rotation 828 into the aperture 836 of the gantry 804. The object's shape is analyzed (step 1004). The location of the wedges 822 of the dynamic bowtie filter 820 as a function of time in the scan is determined (step 1008). The wedges 822 begin to move according to the shape of the object 832 and the desired wedge locations over time (step 1012). The x-ray source 816, dynamic bowtie filter 820, and x-ray detector 824 are rotated around the axis of rotation 828 (step 1016). The x-ray source 816 provides x-rays (step 1020). The x-rays are passed through the dynamic bowtie filter 820 (as it changes over time) and object 832 (step 1024) while the gantry rotates. The x-rays are detected at the detector (step 1028). An image is created from the detected x-rays (step 1032). The image is displayed (step 1036).

FIG. 11 is a schematic perspective view of a wedge 822 attached to an actuator 1104. In this embodiment the actuator 1104 moves the wedge 822 in a direction perpendicular to the length of the cross-section collimated x-ray beam. In this embodiment, since the direction perpendicular to the length of the cross-section of the x-ray is parallel or substantially parallel to the axis of rotation 828 and the movement of the support 808, the actuator 1104 moves the wedge 822 parallel or substantially parallel to the axis of rotation 828 and the movement of the support 808. The wedges 822 increase or decrease in thickness along the direction of the movement by the actuators 1104. The movement by the actuator 1104 increases or decreases the cross-section of the wedge 822 through which the fan shape x-ray passes, thus dynamically changing the bowtie filter shape. In this embodiment, a first direction F is a direction of movement by the actuator that is away from the actuator. The thickness T of the wedge decrease along the first direction. In addition, a direction X is along a path from the x-ray source to the object. The width of the wedge W as seen by the x-ray beam at location X increases as the wedge is moved in the direction of the arrow. As shown in FIG. 2A, the thicknesses of the wedges in the first and second row decrease in the first direction.

Additional Embodiments

Location Measurement

An embodiment of the invention focused on the use of the dynamic bowtie to enable photon counting detectors. However, another embodiment may use traditional energy-integrating detectors and the dynamic bowtie to control radiation dose. The fundamental ability granted by the dynamic bowtie is to customize the distribution of radiation to the imaging task, and the addition of the dynamic bowtie would enable region-of-interest scans and would allow CT scanners to reduce the radiation to sensitive organs. Prior experiments with the virtual dynamic bowtie, relevant to inverse geometry systems, suggest that the magnitude of this dose efficiency improvement can be quite large. Other embodiments of the invention may provide increased or decreased complexity of the bowtie design, by adding more actuators or faster motors. Other embodiments of the invention are designed for controlling variations in the z-direction or to reduce the detected scatter-to-primary ratio. An actuator may drive many wedges or each wedge may have its own actuator.

In some cases, only imaging of a known fraction of the cross-section of the object may be needed. For example, when imaging the heart, the image quality in other parts of the cross-section may not need to be high while it may be desirable to reduce the radiation dose to those other regions (e.g., the breast). In such cases, the dynamic bowtie can be used to substantially reduce the x-ray flux in rays that do not pass through the needed portions and thereby protect the other parts from radiation.

As mentioned above, it is important that the location of the wedges be known; otherwise the dynamic bowtie may produce artifacts. The lack of precision in the actuator may result in error in the amount of attenuation produced by the dynamic attenuation profile, and this error will propagate into the reconstruction. A real-time sensing method can eliminate this source of error.

Figure 13:
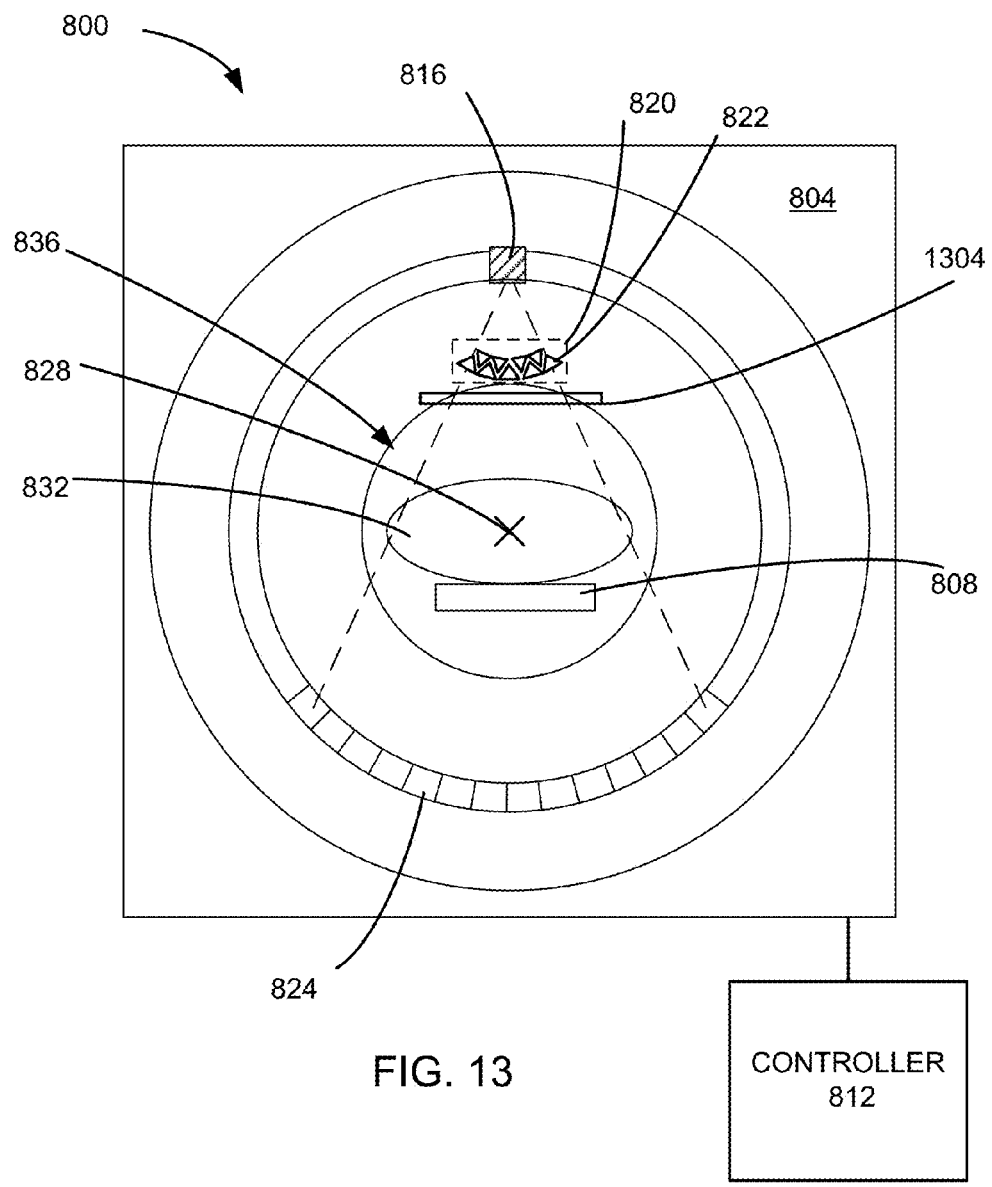
FIG. 13 is a schematic end view of a CT system comprising a gantry, a support, a dynamic bowtie filter, a controller, and a thin detector.

In some embodiments of the invention, calibrating the dynamic bowtie is provided by determining, with great precision, the location of the individual wedges of the bowtie and the provided attenuation profile. In one embodiment, actuators provide a very high level of precision. In another embodiment, location systems, such as an optical tracking system, are used to determine the location of the wedges. FIG. 12 schematic perspective view of a wedge 822 and actuator 1104. An optical system 1204, such as an interferometer is used to accurately measure the location of the wedge 822 by reflecting a beam of light 1208 on the wedge 822. In another embodiment, a thin detector could be used to determine the pre-patient attenuation profile. A "thin detector," is a detector placed between the dynamic bowtie and the patient, which would absorb and detect only a small fraction of the photons that pass through it, allowing most of the flux to be used on the patient. The thin detector would then provide a direct measure of the flux profile that is incident on the patient. FIG. 13 is a schematic end view of a CT system comprising a gantry 804, a support 808, a dynamic bowtie filter 820, a controller 812, and a thin detector 1304. In one embodiment, only a single line of detectors (rather than an area detector) could be used. In such an embodiment, the detector could be displaced off-center, into a region that would otherwise be collimated, and then the detector could be made thick (that is, absorb more of the photons incident on it) because they would be collimated anyway. With the thick line detector, the flux profile everywhere else would be inferred rather than directly measured. The optical tracking system would likewise determine the location of the wedges, and the flux profile would then be inferred from the wedge locations.

Because the entire x-ray source assembly is subject to mechanical instabilities, it is important to determine the locations of the wedges as perceived by the detector. Neither the thin detector nor the optical tracking system can provide such "absolute locations," meaning the locations as perceived by the detector. They provide only relative locations, meaning that in the presence of mechanical instabilities (such as a slight rotation of the bowtie or source assembly), they cannot provide an accurate depiction of the flux profile on the detector. To resolve the absolute locations of the wedges, another embodiment of the invention uses high-contrast markers. These high-contrast markers could be, for example, small beads of an appropriately attenuating metal (for example, tungsten) that are embedded within the wedges at known positions. These beads will cast a shadow on the detector, and the locations of the shadows would be used to determine the position of the wedges. The high-contrast markers could modestly degrade the quality of the data that lie in the shadow of the marker, so as one option, the high-contrast markers could only be used on the outermost wedges, so that the shadows of the high-contrast markers would usually not overlap with the shadow of the patient (unless the patient is large). Once the high-contrast markers have been used to provide the location of some of the wedges, the relative position could then be determined by an optical tracking system or any other concept thus far described. FIG. 14 is a schematic view of a wedge 822 with an actuator 1104 and a high contrast marker 1404.

Wedge Design for a Smooth (Continuous in Derivative) Attenuation Profile

The sharp corners in the dynamic piecewise-linear attenuation profile may also cause errors because of interactions with focal spot drift. By "sharp corners," we mean that the derivative in the piecewise-linear profile is discontinuous. Some embodiments of the invention alleviate these artifacts and real-world imperfections.

The piecewise-linear attenuation profile in previously described embodiments of the invention has the advantage of being continuous. This continuity will reduce some immediate artifacts, such as those resulting from the nonzero focal spot size. However, the piecewise-linear attenuation profile is discontinuous in its derivative, which may cause problems when the system is subject to focal spot drift or motion.

Other embodiments have alternative wedge shapes which are not discontinuous in the derivative or which may have other advantages. Fundamentally, the wedge shapes only need to form a mathematical basis for the functions to be used in an embodiment. Other embodiment may use more complicated splines, or the function could be piecewise-quadratic rather than piecewise-linear.

In an embodiment of the invention, wedge designs produce an attenuation profile that is close to piecewise-linear, but do not suffer from the derivative-discontinuous transitions. One embodiment is to smooth the triangular cross-sections by convolving them with a smoothing function such as a Gaussian. Another embodiment is to round the corners of the triangle or to modify them in such a way that the resulting attenuation profile becomes continuous in the derivative. FIG. 15 is a top view of a wedge 1504 that has a more Gaussian shape. The central corner 1508 is rounded. The sides near the outer corners 1512 are curved to provide a more Gaussian shape.

In other embodiments different wedge shapes are possible that are not limited to an attenuation profile that is piecewise-linear. Piecewise-linearity has the advantage of being simple, and some of the above embodiments provide a variation of our previously described piecewise-linear design which would produce similar attenuation profiles but be continuous in the derivative.

In an embodiment of the invention, the actuators move the wedges as the actuators and wedges are rotated around the object. In one embodiment, the movement by the actuators during rotation accommodates the rotational position of the x-ray source and dynamic bowtie filter with respect to the object. In one embodiment, the movement is preprogrammed in relation to the rotational position based on data acquired from the object or on prior knowledge or assumed shape of the object. In another embodiment, an analysis of the object and measured by the actual measured projections governs in real time how the wedges are actuated during rotation.

In one embodiment, the dynamic movement, actuation of the wedges during rotation, is for evening out noise. In another embodiment, the dynamic movement is for imaging one or more specific areas of interest, while ignoring other areas.

One of the critical challenges with the dynamic attenuator is the question of calibration. The locations of the wedges must be quite precisely known so that the radiation exposure profile incident on the patient can be estimated. Other embodiments provide additional methods for detecting the location of the wedges.

FIG. 16 is a schematic view of a wedge 822 with an actuator 1104 used in another embodiment. In this embodiment, a series of markings (such as dots) 1604 are placed on each wedge 822, and an optical sensor 1608, such as a camera, is placed used to detect the location of each of the markings 1604. The location of each mark could then be calibrated to the location of each wedge. The resolution of this method is dependent on the resolution of the optical sensor, but a much higher sensitivity is provided by using multiple markings 1604 on each wedge 822. The locations of the series of markings 1604 may be converted using the calibration data to a location of the wedge. An average can be used to reduce noise. In other embodiments, the optical sensor 1608 is a 1D sensor array, which may be preferred for its high speed and low cost. If the optical sensor 1608 is a 1D sensor array, the series of marking 1604 would be a striped pattern which would indicate the wedge's location.

FIG. 17 is a schematic view of a wedge 822 with an actuator 1104 used in another embodiment. A light source system 1704, such as a laser system or more generally some form of structured light creates a light beam 1706, which creates a light spot 1708 on the wedge 822. An optical sensor 1712 detects to location of the light spot 1708. For example, a laser dot could be used to triangulate the position of the wedge, in an "active stereo" setup. To create a light spot 1708 on a plurality of wedges, the light source system 1704 in one embodiment would provide a plurality of lasers, where each wedge has a corresponding laser. In another embodiment, a single laser may create a plurality of light beams to illuminate a plurality of wedges.

FIG. 18 is a schematic view of a wedge 822 with an actuator 1104 used in another embodiment. A linear scale 1804 is placed on a shaft 1806 extending from the actuator 1104 to the wedge 822. A linear encoder 1808 is placed in a position so that the linear encoder 1808 is able to sense the linear scale 1804. In this embodiment, the linear encoder 1808 is an optical linear encoder. The linear scale 1804 is an optical encoder pattern. In other embodiments a magnetic linear encoder is used with a magnetic linear scale. In other embodiments, the linear scale is attached directly to the wedge. A magnetic sensor array could similarly be used.

In an embodiment each wedge may have an optical sensor, so that a plurality of wedges has a plurality of optical sensors, wherein the plurality of optical sensors forms an optical sensor system.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A CT apparatus for scanning an object, comprising:
an x-ray source, wherein the x-ray source provides a collimated x-ray beam with a cross-section with a length and thickness;
a plurality of wedges between the source and object;
an actuator connected to a wedge of the plurality of wedges for moving the wedge in a direction of movement substantially perpendicular to the length of the cross-section of the collimated x-ray beam;
an x-ray detector on an opposite side of the object from the x-ray source for detecting x-rays that pass through the object and the plurality of wedges;
a gantry for rotating the x-ray source, the plurality of wedges, and the x-ray detector around an axis of rotation, wherein the actuator moves the wedge of the plurality of wedges in a direction of movement substantially parallel to the axis of rotation and wherein each wedge of the plurality of wedges increases or decreases in thickness along the direction of movement and wherein the length of the cross-section is defined as being perpendicular to the direction of movement wherein thicknesses of each wedge of the plurality of wedges change in a direction along the length of the cross-section of the collimated x-ray beam which is perpendicular to the direction of movement and wherein the thicknesses of the wedges increase or decrease in a direction that is perpendicular to the direction of movement and the length of the cross-section of the collimated x-ray beam; and
a detection system, which measures relative positions of the plurality of wedges, wherein the detection system, comprises:
an optical sensor; and
a plurality of optical markers, wherein each wedge of a first plurality of wedges of the plurality of wedges has at least one optical marker of the plurality of markers attached.

2. The CT apparatus, as recited in claim 1, wherein each wedge of the first plurality of wedges has a plurality of attached optical markers.

3. The CT apparatus, as recited in claim 2, wherein the plurality of attached optical markers on each wedge forms a 2 D grid.

4. The CT apparatus, as recited in claim 2, wherein the plurality of optical markers forms an optical encoder pattern.

5. The CT apparatus, as recited in claim 2, wherein the optical sensor comprises a plurality of optical sensing devices, wherein each wedge of the first plurality of wedges has an optical sensing device of the plurality of optical sensing devices.

6. The CT apparatus, as recited in claim 2, wherein each wedge of the plurality of the first plurality of wedges is moved by a shaft, wherein the attached optical markers are attached to the shaft.

7. The CT apparatus, as recited in claim 1, wherein the optical sensor is a camera for generating an image.

8. The CT apparatus, as recited in claim 1, wherein the plurality of wedges comprises:
 a first row of wedges; and
 a second row of wedges, wherein the second row of wedges are placed to overlap with the first row of wedges in a direction from the x-ray source to the object.

9. The CT apparatus, as recited in claim 8, wherein in the first row of wedges, each wedge of the first row of wedges has a thickness that increases in a first direction of movement by the actuators and in the second row of wedges, each wedge of the second row of wedges has a thickness that increases in the first direction.

10. A CT apparatus for scanning an object, comprising:
 an x-ray source, wherein the x-ray source provides a collimated x-ray beam with a cross-section with a length and thickness;
 a plurality of wedges between the source and object;
 an actuator connected to a wedge of the plurality of wedges for moving the wedge in a direction of movement substantially perpendicular to the length of the cross-section of the collimated x-ray beam;
 an x-ray detector on an opposite side of the object from the x-ray source for detecting x-rays that pass through the object and the plurality of wedges;
 a gantry for rotating the x-ray source, the plurality of wedges, and the x-ray detector around an axis of rotation, wherein the actuator moves the wedge of the plurality of wedges in a direction of movement substantially parallel to the axis of rotation and wherein each wedge of the plurality of wedges increases or decreases in thickness along the direction of movement and wherein the length of the cross-section is defined as being perpendicular to the direction of movement wherein thicknesses of each wedge of the plurality of wedges change in a direction along the length of the cross-section of the collimated x-ray beam which is perpendicular to the direction of movement and wherein the thicknesses of the wedges increase or decrease in a direction that is perpendicular to the direction of movement and the length of the cross-section of the collimated x-ray beam; and
 a detection system, which measures relative positions of the plurality of wedges, wherein the detection system, comprises:
  an optical sensor; and
  a laser, which generates a laser light, which illuminates a portion of a wedge of the plurality of wedges, wherein when the wedge is moved in the direction of movement the portion of the wedge illuminated by the laser light moves in a direction different than the direction of movement.

11. The CT apparatus, as recited in claim 10, wherein each wedge of the first plurality of wedges is illuminated by laser light.

12. The CT apparatus, as recited in claim 11, wherein the optical sensor comprises a plurality of optical sensing devices, wherein each wedge of the first plurality of wedges has an optical sensing device of the plurality of optical sensing devices.

13. A CT apparatus for scanning an object, comprising:
 an x-ray source, wherein the x-ray source provides a collimated x-ray beam with a cross-section with a length and thickness;
 a plurality of wedges between the source and object;
 an actuator connected to a wedge of the plurality of wedges for moving the wedge in a direction of movement substantially perpendicular to the length of the cross-section of the collimated x-ray beam;
 an x-ray detector on an opposite side of the object from the x-ray source for detecting x-rays that pass through the object and the plurality of wedges;
 a gantry for rotating the x-ray source, the plurality of wedges, and the x-ray detector around an axis of rotation, wherein the actuator moves the wedge of the plurality of wedges in a direction of movement substantially parallel to the axis of rotation and wherein each wedge of the plurality of wedges increases or decreases in thickness along the direction of movement and wherein the length of the cross-section is defined as being perpendicular to the direction of movement wherein thicknesses of each wedge of the plurality of wedges change in a direction along the length of the cross-section of the collimated x-ray beam which is perpendicular to the direction of movement and wherein the thicknesses of the wedges increase or decrease in a direction that is perpendicular to the direction of movement and the length of the cross-section of the collimated x-ray beam; and
 a detection system, which measures relative positions of the plurality of wedges, wherein the detection system, comprises:
  a magnetic sensor system; and
  a plurality of magnetic markers, wherein each wedge of a first plurality of wedges of the plurality of wedges has at least one magnetic marker of the plurality of markers attached.

14. The CT apparatus, as recited in claim 13, wherein the magnetic sensor system comprises a plurality of magnetic sensing devices, wherein each wedge of the first plurality of wedges has a magnetic sensing device of the plurality of magnetic sensing devices.

* * * * *